United States Patent [19]

Avar

[11] Patent Number: 5,489,632
[45] Date of Patent: Feb. 6, 1996

[54] IMINO ETHERS

[75] Inventor: Lajos Avar, Biel-Benken, Switzerland

[73] Assignee: Sandoz Ltd., Basle, Switzerland

[21] Appl. No.: 98,975

[22] Filed: Jul. 28, 1993

[30] Foreign Application Priority Data

Jul. 30, 1992 [GB] United Kingdom ............... 9216191

[51] Int. Cl.$^6$ ............... C08K 5/3438; C08K 5/3447; C08K 5/45; C08K 5/3492
[52] U.S. Cl. ............... 524/84; 524/91; 524/100; 524/241; 544/215; 544/216; 546/202; 546/216; 546/242; 548/260; 549/58; 549/75; 549/76; 549/77; 558/302
[58] Field of Search ............... 544/215, 216; 546/202, 216, 242; 548/260; 549/58, 75, 76, 77; 558/302; 524/84, 91, 100, 241

[56] References Cited

U.S. PATENT DOCUMENTS

| 4,863,802 | 9/1989 | Moore | 428/412 |
|---|---|---|---|
| 5,021,478 | 6/1991 | Ravichandran | 524/91 |
| 5,106,891 | 4/1992 | Valet | 524/91 |
| 5,194,456 | 3/1993 | Gupta | 523/106 |
| 5,229,512 | 7/1993 | Slongo | 544/215 |

FOREIGN PATENT DOCUMENTS

| 0386298 | 9/1990 | European Pat. Off. . |
|---|---|---|
| 0389427 | 9/1990 | European Pat. Off. . |
| 0431868 | 6/1991 | European Pat. Off. . |
| 0453396 | 10/1991 | European Pat. Off. . |
| 0453405 | 10/1991 | European Pat. Off. . |

OTHER PUBLICATIONS

Search Report—France—dated 13 Apr. 1995 for FR 9309207.
Derwent Abstracts of: EP 0431868; EP 0389427; EP 0453396; EP 0386298; EP 0453405.

*Primary Examiner*—Kriellion S. Morgan
*Attorney, Agent, or Firm*—Robert S. Honor; Carl W. Battle; Gabriel Lopez

[57] ABSTRACT

Novel imino ether compounds, processes for their production and methods for their use are provided. These novel imino ether compounds are particularly useful as light stabilizers for polymeric compositions, particularly for lacquer coating compositions.

13 Claims, No Drawings

IMINO ETHERS

The invention relates to new imino ethers, their preparation and their use as light stabilisers for polymeric material.

According to the invention there is provided a compound of formula I $$[Y]\left[\begin{array}{c}-C=N-\\|\\O-X\end{array}\right]_n[Z]$$

in which $n$ is 1, 2 or 3;

Y is $C_{1-22}$alkyl or phenyl, unsubstituted or monosubstituted by phenyl and/or mono-, di- or tri-substituted by $C_{1-4}$alkyl, $C_{1-4}$alkoxy and halogen; or Y is

[thiophene and benzothiophene structures]

Z, when n is 1, is $C_{1-22}$alkyl, uninterrupted or interrupted by —O— (preferably uninterrupted) or phenyl unsubstituted or substituted by 1 to 3 groups selected from $C_{1-4}$alkyl, $C_{1-4}$alkoxy and halogen and/or by one group phenyl;

Z, when n is 2, is $C_{1-22}$alkylene uninterrupted or interrupted by —O— (preferably uninterrupted) or phenylene, unsubstituted or monosubstituted by a $C_{1-4}$alkyl, $C_{1-4}$alkoxy or halogen group; and Z, when n is 3, is a trivalent $C_{1-22}$alkane group or a group of the formula

[trisubstituted benzene structure]

X is a group of formula α, β, γ or δ

[structure α: 2-hydroxybenzophenone]

[structure β: 2-(2-hydroxyphenyl)benzotriazole]

[structure γ: tris-aryl triazine with OH]

[structure δ: hindered amine (HALS) structure with $R_1$, $R_2$, $R_9$, N—R]

in which

R is hydrogen; oxygen; —OH; $C_{1-24}$alkyl; —O—CO—$C_{1-24}$alkyl; —O—$C_{1-24}$alkyl; —O—CO-phenyl or —COR$_5$;

where $R_5$ is -C($R_3$)=CH$_2$, $C_{1-6}$alkyl, phenyl, —COC$_{1-24}$alkyl; —CO-phenyl, —NR$_7$R$_8$, —CH$_2$—C$_6$H$_5$, —CO—OC$_{1-12}$alkyl or —COOH; $R_3$ is hydrogen or $C_{1-4}$alkyl, $R_7$ is hydrogen, $C_{1-12}$alkyl, $C_{5-6}$cycloalkyl, phenyl, phenyl-$C_{1-4}$alkyl or $C_{1-12}$alkylphenyl and $R_8$ is $C_{1-12}$alkyl or hydrogen, each $R_1$ independently, is —CH$_3$ or —CH$_2$(C$_{1-4}$alkyl) or both groups $R_1$ from a group —(CH$_2$)$_5$—;

each $R_2$, independently, is —CH$_3$ or —CH$_2$(C$_{1-4}$alkyl) or both groups $R_2$ form a group —(CH$_2$)$_5$—;

each $R_4$, independently is hydrogen, $C_{1-22}$alkyl, $C_{1-22}$alkoxy or halogen; and $R_9$ is a direct bond or divalent bridging group.

Preferably R is R' where R' is hydrogen, $C_{1-4}$alkyl or —CO—R$_5$' where R$_5$' is —CH=CH$_2$, $C_{1-4}$alkyl or —CO—O—$C_{1-4}$alkyl.

Preferably each $R_1$ and each $R_2$ is —CH$_3$.

Preferably Y is attached to the C atom and 7 is preferably attached to the N atom in formula I Preferably X is X' where X' is a group of the formula γ.

Preferably Y is Y' where Y' is $C_{1-22}$alkyl or phenyl.

Preferably Z is Z' where Z', when n=1, is $C_{1-12}$alkyl or a group of the formula

[phenyl-$R_{10}$ structure]

where Z', when n=2, is $C_{1-8}$alkylene or a group of the formula

[phenylene structure]

where Z', when n=3, is a group of the formula

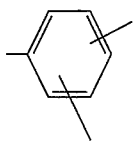

where $R_{10}$ is methyl, ethyl, methoxy, ethoxy, chloro or phenyl.

Preferably n is n' where n' is 1 or 2

Preferably $R_9$ is $R_9'$ where $R_9'$ is a direct bond or

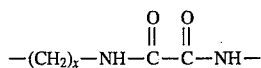

where x is 1 to 8.

In this Specification any $C_{1-22}$alkyl is preferably $C_{1-4}$alkyl and any $C_{1-4}$alkyl group is preferably methyl or ethyl; preferably any alkoxy group is methoxy or ethoxy.

In this Specification, any group capable of being linear or branched is linear or branched.

Where a symbol appears more than once in a formula, its significances are independent of one another.

A compound of formula I can be prepared by reacting 1 mole of a compound of formula II

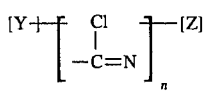 (II)

with n moles of a compound of formula III

X—OH                    (III)

where the symbols are as defined above, at a reduced temperature.

Further, according to the invention there is provided a composition comprising a polymeric material and a compound of formula I defined above. Further, according to the invention there is provided a method for stabilising a lacquer composition based on acrylic, alkyd or polyester resins (which, if desired can be crosslinked with melamine/formaldehyde resins, epoxide resins or polyisocyanates) which comprises incorporating into the resin one or more compounds of formula I as defined above.

Further, according to the invention there is provided a lacquer composition based on acrylic, alkyd and/or polyester resins (which if desired, can be crosslinked with melamine/formaldehyde resins, epoxide resins or polyisocyanates) containing one or more compound of formula I as defined above.

The concentration of compound of formula I employed in the polymeric material is suitably 0.01 to 8% by weight, preferably 0.02 to 1% by weight and gives a clear improvement in the light- and weather-stability of organic pigments in stoving finishes as well as reducing the tendency to hairline cracking and loss of gloss as the result of weathering. This is also found for metallic finishes and excellent long-term stability of the clear top coat of two layer metallic finishes is obtained. In such finishes, the compound of formula I may be added to the metallic undercoat, the clear top coat or both, preferably only to the clear top coat. The metal surface to be finished may be under-coated with primer coatings as is customary in the art of coating metal surfaces.

The compound or compounds of formula I may be added before, during or after the polymerization step, and may be added in solid form; in solution, preferably as a liquid concentrate containing from 20 to 80% by weight of compound of formula I and 80–20% solvent; or as a solid masterbatch composition containing 10 to 80% by weight of compound of formula I and 90 to 20% by weight of a solid polymeric material which is identical with or compatible with the polymeric material to be stabilized.

Suitable polymeric materials include plastic materials for example polyethylene, polypropylene, ethylene/propylene copolymers, polyvinyl chloride, polyester, polyamide, polyurethane, polyacrylonitrile, ABS, terpolymers of acrylates, styrene and acrylonitrile, styrene/acrylonitrileand styrene/butadiene. Other plastics material such as polybutylene, polystyrene, chlorinated polyethylene, polycarbonate, polymethylmethacrylate, polyphenylene oxide, polypropylene oxide; polyacetals, phenol/formaldehyde resins and epoxy resins may also be used. Preferred plastic materials are polypropylene, polyethylene, ethylene/propylene copolymers and ABS. Natural polymers for example natural rubber may also be stabilized, as may lubricating oils containing polymeric material.

The compounds of formula I may be incorporated by known methods into the polymeric material to be stabilized. Of particular importance is blending of the compounds with thermoplastic polymers in the melt, for example in a melt blender or during the formation of shaped articles, including foils, films, tubes, containers, bottles, fibres and foams by extrusion, injection moulding, blow moulding, spinning or wire coating.

It is not essential for the polymeric material to be fully polymerised before mixing with the compounds according to the invention. The compounds may be mixed with monomer, prepolymer or precondensate, and the polymerisation or condensation reaction is carried out subsequently. This will of course be the preferred method of incorporation of the compounds into thermosetting polymers, which cannot be melt blended.

Further additives that can be added to polymeric compositions according to the invention include aminoaryl compounds, U.V. stabilisers and antistatic agents, flameproofing agents, softeners, nucleating agents, metal deactivators, biocides, impact modifiers, fillers, pigments and fungicides.

Preferred aminoaryl compounds include N,N'-dinaphthyl-p-phenylene diamine and N,N'-hexamethylene-bis-3-(3,5-ditert.butyl-4-hydroxy phenyl)-propionamide.

Preferred U.V. stabilisers include U.V. absorbers (e.g. 2-(2'-hydroxyphenyl) benztriazoles, 2-hydroxybenzophenones, 1,3-bis-(2'-hydroxy benzoyl)benzene salicylates, cinnamates and oxalic acid diamides; U.V. quenchers such as benzoates and substituted benzoates; and hindered amine light stabilisers (for example N-unsubstituted, N-alkyl or N-acyl substituted 2,2,6,6-tetra-alkylpiperidine compounds) other than those of the invention.

Further antioxidants can be added to polymeric material either before, at the same time as or after (but before polymerisation occurs) the addition of a compound according to the invention.

Examples of antioxidants include benzofuran-2-ones, indolin-2-ones and sterically hindered phenols, sulphur and phosphorus containing compounds and mixtures thereof.

Preferred sterically hindered phenols include β-(4-hydroxy-3,5 ditert.butylphenyl)-propionyl stearate,methane-tetrakis-(methylene-3(3',5'-ditert.butyl-4-hydroxy-phenyl)-propionate),1,3,3-tris-(2-methyl-4-hydroxy-5-tert.butylphenyl) butane, 1,3,5-tris(4-tert.butyl-3-hydroxy-2,6-di-methylbenzyl)-1,3,5-triazinyl-2,4,6(1H,3H,5H)trione, bis-(4-tert.butyl-3-hydroxy-2,6-di-methylbenzyl)dithiol terephthalate, tris(3,5-ditert.butyl-4-hydroxybenzyl) isocyanurate, the triester of beta-(4-hydroxy-3,5-ditert.butylphenyl) propionic acid with 1,3,4-tris-(2-hydroxyethyl)-5-triazinyl-2,4,6(1H,3H,5H)-trione,bis(3,3-bis-(4'-hydroxy-3-tert.butylphenyl)butyricacid)glycol ester, 1,3,5-trimethyl-2,4,6-tris-(3,5-ditert.butyl-4-hydroxybenzyl) benzene, 2,2'-methylene-bis-(4-methyl-6-tert.butylphenyl)terephthalate,4,4-methylene-bis-(2,6-ditert.-butylphenol), 4,4'-butylidine-bis-(tert.butylmetacresol), 2,2'-methylene-bis-(4-methyl-6-tert.-butyl)-phenol, 1,3,5-tris-(3,5-di-t-butyl-4-hydroxyphenyl)-isocyanurate and 1,1,3,tris-(5-tert.butyl-4-hydroxy-2-methylphenyl)-butane.

Preferred sulphur containing antioxidative co-stabilizers which may be used include di-tridecyl-3,3-thiodipropionate, distearyl-3,3-thiodipropionate, di-lauryl-3,3-thiodipropionate, methane tetrakis (methylene-3-hexylthiopropionate), methane tetrakis (methylene-3-dodecylthiopropionate) and dioctadecyl disulphide.

Preferred phosphorus-containing co-stabilizers which may be used include trinonylphenyl phosphite,4,9-distearyl-3,5,8,10-tetraoxa-diphosphaspiroundecane, tris-(2,4-ditert-.butyl-phenyl) phosphite, trilauryl phosphite, bis(2,6-di-t.butyl-4-methylphenyl)pentaerythrityl-diphosphite, bis(2,4-di-t.butylphenyl) pentaerythrityl-diphosphite, distearyl-pentaerythrityl diphosphite and tetrakis(2,4-ditert.butyl phenyl)-4,4'-biphenylene diphosphonite.

Further additives that can be added to polymeric compositions according to the invention include aminoaryl compounds, U.V. stabilisers and antistatic agents, flameproofing agents, softeners, nucleating agents, metal deactivators, biocides, impact modifiers, fillers, pigments, and fungicides.

Preferred aminoaryl compounds include N,N'-dinaphthyl-p-phenylene diamine and N,N'-hexamethylene-bis-3-(3,5-ditert.butyl-4-hydroxy phenyl)-propionamide.

Preferred U.V. stabilisers include U.V. absorbers (e.g. 2-(2'-hydroxyphenyl)-benztriazoles, 2-hydroxybenzophenones,1,3-bis-(2'-hydroxy-benzoyl-)benzene salicylates, cinnamates and oxalic acid diamides; U.V. quenchers such as benzoates and substituted benzoates; and hindered amine light stabilisers (for example N-unsubstituted, N-alkyl or N-acyl substituted 2,2,6,6-tetra-alkyl piperidine compounds) other than those of the invention.

Preferably a compound of formula XX

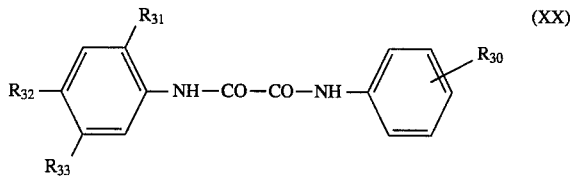

in which $R_{30}$ is $C_{6-22}$alkyl or $C_{6-22}$alkoxy;

$R_{31}$ and $R_{32}$ independently, are selected from hydrogen, $C_{1-8}$alkyl, $C_{1-12}$alkoxy, $C_{1-12}$alkylthio, phenoxy and phenylthio provided that only one of $R_{31}$ and $R_{32}$ is alkylthio, phenoxy or phenylthio; and $R_{33}$ is hydrogen or $C_{1-8}$alkyl; is added to a compound of formula I.

The compounds of formula I are especially suitable for use in organic polymer-containing coatings, particularly automotive finishes.

Automotives finishes are generally solutions or dispersion of organic polymers or polymer precursors in organic solvents. The majority are stoving finishes, which require the application of heat, generally above 80° C., on order to harden the finish in an acceptable time once it has been applied to the primer-coated metal surface. The hardening step may be accelerated by the use of an acid catalyst. The effect of this heating may be to accelerate the chemical reaction between polymer precursors in a thermosetting system, or to bring about fusion of particles of a thermoplastic polymer.

Many automotive finishes are metallic finishes, which contain flakes of metal, usually aluminium, in order to provide optical effects due to reflection. Such finishes are often two-coat finishes, in which a clear top coat finish is applied over a base coat finish containing a single pigment and/or metal flakes. The compounds of formula I can be in the top coat finish or the ground coat finish, preferably the former. Such two-coat metallic finishes have particular need to U.V.-stabilizers in the top coat, since the polymer in this coat is not protected by light-absorbing pigments, and it is subjected to almost double the normal amount of radiation because of reflection of light from the lower metallic layer.

The compounds of formula I are suitable for use as U.V.-stabilizers in a wide range of liquid finishes, for example those based on combinations of melamine-formaldehyde resins with oil-modified polyester resins, polyacrylate resins with added crosslinkers, or saturated polyesters; or on self-crosslinked polyacrylate or polyacrylate resin co-polymerised with styrene.

Further examples are two-component finishes based on an aliphatic or aromatic di-isocyanate and a hydroxy-group-containing polyacrylate, polyester or polyether resin. These polyurethane 2-component finishes are preferably hardened at 60° to 120° C. Thermoplastic polyacrylate resins may also be used, the latter being particularly useful in metallic finishes, as are also polyacrylate resins with added crosslinkers in combination with melamine-formaldehyde resins etherified with butanol and, further hydroxy-group-containing polyacrylate resins are described in U.S. Pat No. 3,062, 753, the contents of which are incorporated herein by reference.

The compounds of formula I are particularly useful in acid catalysed stoving finishes particularly in the top coat of two metallic finishes.

The compounds of formula I may be added to the finish at any stage in its manufacture, and may be added in solid form or in a solution, preferably in the form of a liquid concentrate in a suitable solvent or in the form of a dispersion in water or organic solvent.

In practice the compounds of formula I are added to a finish as a solution in organic solvent (as a liquid finish) in which the binder material is between 35% (low solid finishes) and 70% by weight (high solid finishes). The binder material of the finish can be in aqueous emulsion or suspension form (as an aqueous finish) in which material part makes up 20 to 30% by weight. However, the compounds of formula I can be added to known powder finishes.

The compounds of formula I are to be added to the liquid or powder finishes before stoving or hardening. Preferably the compounds of formula I are used in liquid finishes since it is easy to add exact dosages. It is particularly preferred to use a concentrate (preferably in a hydrocarbon solvent) containing at least 40% preferably 60 to 80% by weight of the total weight of the concentrate of compound of formula I to finishes for stoving.

The compounds of the invention can also be used in photopolymeric substrates containing photoinitiators for the photopolymerisation.

The new stabilizer compositions are especially suitable for use in polyolefins and especially α-polyolefins prepared using processing catalysts known as Generation II to to Generation V catalysts and which have not been subjected to a catalyst removal step. By the term "catalyst removal step" used herein is meant a step for the purpose of positively removing the catalyst residues contained in the polymerized polyolefins or treating the polyolefins with the compound which can react with the catalyst residue and inactivate or solubilize the residue, such as alcohols or water, and then removing the inactivated or solubilized catalyst residue by physical means such as filtration, washing, and centrifuging. Thus, in the case of suspension polymerization, the step of separating the resulting polymer from a dispersion medium, such as a solvent or a liquefied monomer, does not fall under the above-mentioned definition of the catalyst residue removal step, although the catalyst dissolved in the dispersion medium may be removed by a separation step.

The step of adding a small amount of catalyst poisons such as ethers, alcohols, ketones, esters and water to the resulting polymer, to inactivate the catalyst remaining after the completion of polymerization, or the step of treating the resulting polymer suspension with gas such as steam or nitrogen to remove the dispersion medium also does not fall under the above-mentioned definition of the "catalyst residue-removal" step.

What we mean by Generation I catalysts are titanium halide catalysts and an organo aluminium compound or an organo aluminium halide.

What we mean by Generation II catalysts are Generation I catalysts supported on an organo magnesium compound or based on an organo chromium compound supported on SIO2.

randomly distributed along the polymer chain (so called antisotactic polypropylene) or stereoirregular stereoblock polymers. Due to the rapid progress in the development of newer generation catalyst systems the commercial significance of these polymers with novel, highly interesting properties increases more and more. However, residues of such further catalyst generations, as long as they contain metals of the 3d, 4d and 5d series of the periodic system supported analogously to the earlier catalyst generations, can also cause disadvantageous properties in the polymer, as long as such residues are still present in the polymer even if in a deactivated form.

Due to this, it can therefore be expected that the new compositions according to the invention are also suitable for overcoming such disadvantageous properties of the polymer. This means that any disadvantageous interaction between processing stabilizers and the aforementioned residues of catalysts of further generations, particularly the hydrolysis of phosphites and phosphonites, is most effectively inhibited.

These generations of catalysts are described in the Twelfth Annual International Conference on Advances in the stabilization and Controlled Degradation of Polymers held in Luzern, Switzerland, 21–23 May 1990 in an article on pages 181 to 196 inclusive by Rolf Mülhaupt entitled "New Trends in Polyolefin Catalysts and Influence on Polymer Stability". The contents of this article is incorporated herein by reference and especially Table I on page 184 describing the Generation of Catalysts:

TABLE I

| | Polyolefin Catalyst Evolution | | | |
|---|---|---|---|---|
| Generation Example | Cat.Act. (g/PP/gTi h atm) | % Act.Ti | Stereoreg. (% insolin heptane) | Process Technology |
| I. TiCl$_4$/AlR$_3$ | 40 | 0.01 | 45% | removal of cat.residues and atactic PP |
| TiCl$_3$/AlEt$_2$Cl | 30 | 0.1 | 92% | removal of catalyst residues |
| II Mg(OEt$_2$)/TiCl$_4$/AlR$_3$ | 40000 | | 50% | no removal of cat.residues |
| SiO$_2$/Cp$_2$Cr | 40000 | HDPE | | (mainly HDPE/LLDPE) |
| III Mod.TiCl$_3$cat. | 5000 | 1 | 95% | no purification |
| MgCl$_2$/TiCl$_4$/AlR$_3$-ester donor | 20000 | 10 | 92% | |
| IV MgCl$_2$/TiCl$_4$/AlR$_3$-silane donor | 40000 | 18 | 99% | no purification no extrusion |
| V Bis-indenyl-TiR$_2$ on (AlCH$_3$O)$_2$ | 40000 | 100 | 99% | novel PPs, narrow MWD | in which R, in Table 1, is an organo group; HDPE is high density polyethylene, LLDPE is linear low density polyethyene, Cp is cyclopentadienyl, Et is ethyl, PP is polypropylene and MWD is molecular weight distribution.

What we mean by a Generation III catalyst is Ziegler type complex catalyst supported on a halogen containing magnesium compound.

What we mean by a Generation IV catalyst is a Generation III catalyst with a silane donor.

What we mean by Generation V catalysts is a bis-indenyl organo titanium compound supported on alumoxane or bis cyclopentadienyl titanium halides activated by aluminum alkyl compound.

Further generations of highly specific catalysts, especially useful for manufacturing highly stereoregular poly-α-olefins, which are presently under development, belong in the sense of the present invention also to the aforementioned generations of supported catalyst systems. Examples for the microstructure of such highly stereoregular polyolefins are given by syndiotactic polypropylene, isotactic stereoblock polymers, isotactic polypropylene containing stearic defects The invention will now be illustrated by the following Examples in which all parts and percentages are by weight and all temperatures are in °C.

EXAMPLE 1

Preparation of a compound of formula 1a

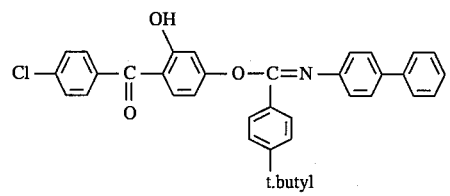

12.4 g of 2,4-dihydroxy-4'-chlorobenzophenone are added to 6.06 g of triethylamine in 100 ml of toluene. A mole equivalent amount of the reaction product of

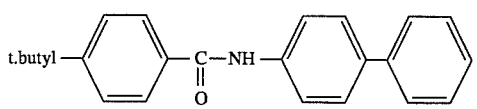

with PCl$_5$ in 100 ml of toluene is added to the benzophenone containing solution at 0° to 1° C. over 15 minutes.

The mixture is left to react for 2 hours at 5° C. then added to water, washed neutral and the solvent is distilled off. The residue is recrystallized out of isopropanol.

A light yellow powder with a melting point of 77°–79° C. results.

EXAMPLES 2 to 17

By a method analogous to Example 1 and from appropriate reactants the following compounds can be prepared:

2. 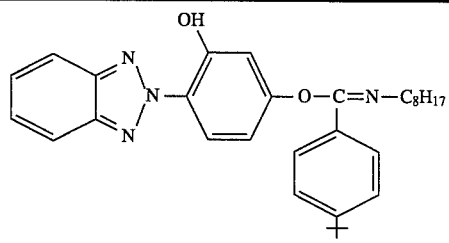

3. 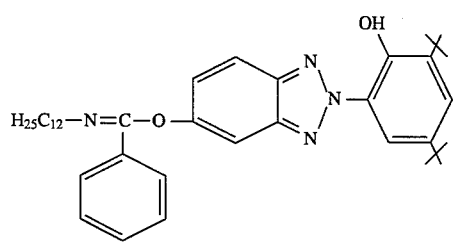

4. 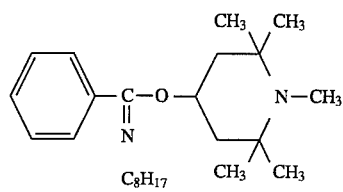

5. 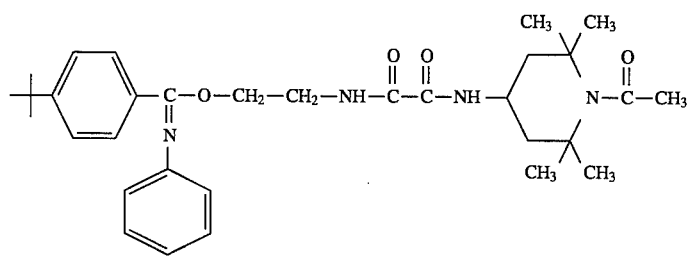

6. 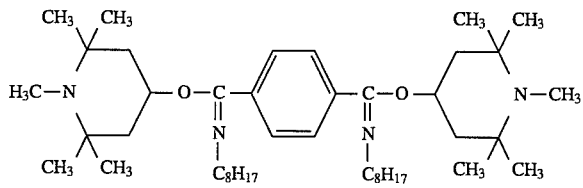

7. 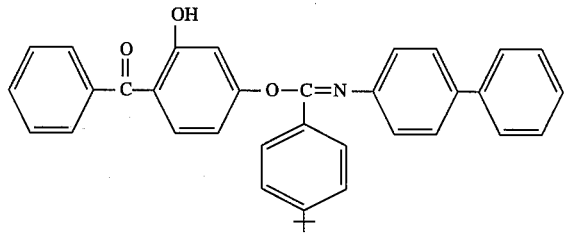

133–134° C.

| | | |
|---|---|---|
| 8. | 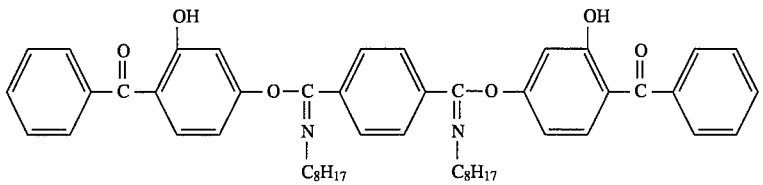 | 95–96° C. |
| 9. | 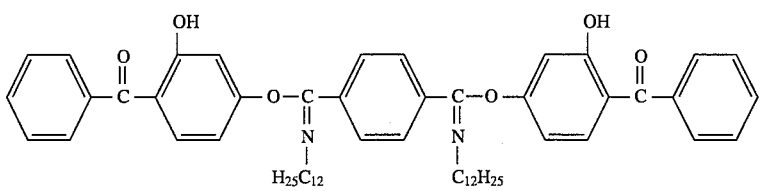 | 78–80° C. |
| 10. | 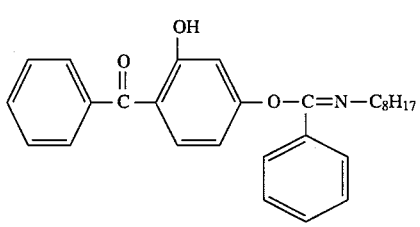 | oil |
| 11. | 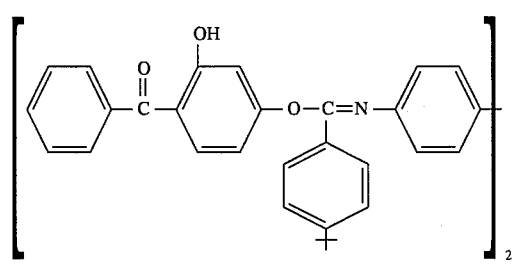 | 184–188° C. |
| 12. | 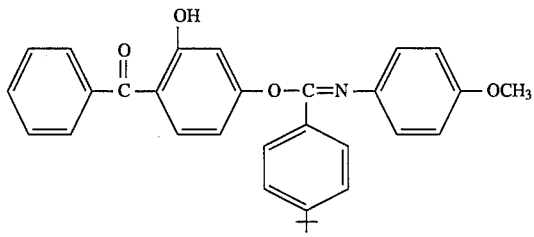 | resin |
| 13. | 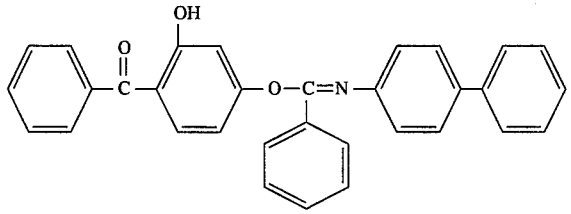 | 153–155° C. |

-continued
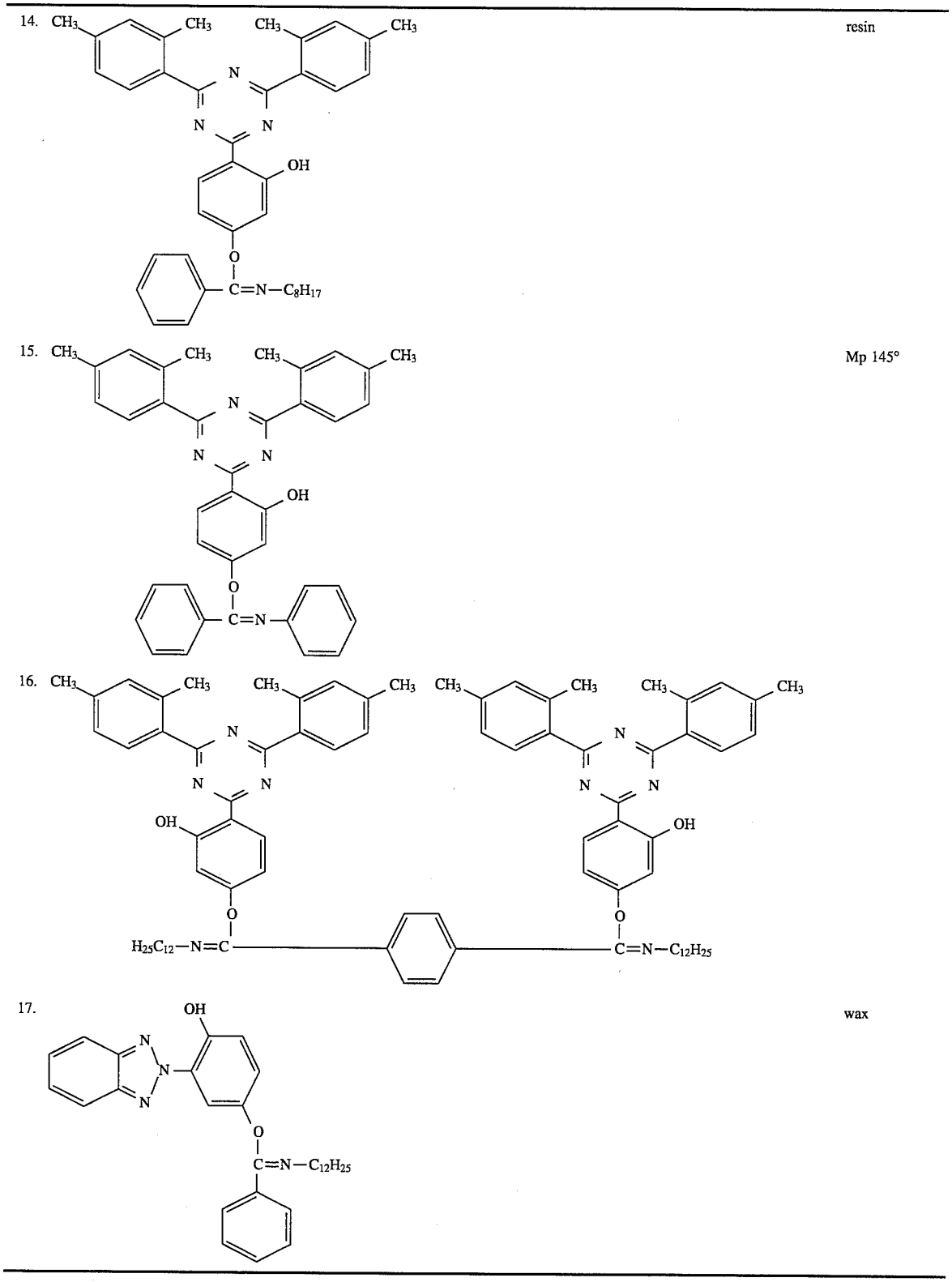
| | |
|---|---|
| 14. | resin |
| 15. | Mp 145° |
| 17. | wax |
APPLICATION EXAMPLE A
A clear finish of
80 Parts of Viacryl SC 344 (a 50% solution of an acryl resin from Vianova),
13.9 Parts of Maprenal MF 80 (a 72% solution of a melamine resin from Hoechst) and
4.1 Parts of Byketol OK (from Byk-Malinckrodt)
is added to 2 parts of a compound of formula 1a (described in Example 1).

After 1 minute the light stabiliser material so formed is dissolved in a finish. The finish is applied conventionally (according to the known 2 layer procedure) to a metallic or single piment finish whilst still wet by spraying to form a layer having a thickness of 30 to 40 μm. The resulting coating is then hardened at 140° C. for 30 minutes. The coating shows very good resistance to U.V. light and weathering.

APPLICATION EXAMPLE B

A clear finish of 29.5 Parts of Setalux C-1502 XX-60 (a 60% solution of an acryl resin from Synthese B.V.), 39.2 Parts of Setalux C-1382 BX-45 (a 45% solution of an acryl resin from Synthese B.V.), 21.4 Parts of Setamine US-138 BB-70 (a 70% solution of a melamine resin from Synthese B.V.), 2.5 Parts of Baysilonoil [(2% solution in Xylene) from Bayer] and 7.4 Parts of Depanol Y (a solvent from Hoechst)

is stirred together with 2.5 parts of a compound of formula 1a (described in Example 1) and 2 parts of an acid catalyst derived from phosphoric acid (Type: Catalyst 269-9 from American Cyanamid) to form a homogeneous mixture.

The finish is applied conventionally (according to known 2 layer procedure) to a metallic or single pigment finish whilst both are still wet by spraying to form a layer having a thickness of 30 to 40 μm. The resulting coating is then hardened at 110° for 20 minutes. The coating shows very good resistance to U.V. light and weathering.

APPLICATION EXAMPLE C

A clear finish of

75 Parts Macrynal SH 510 N (a hydroxy containing acryl resin from Bayer)

2 Parts of Baysilon-oil A [(1% solution in xylene) from Bayer]

0.3 Parts of dibutyl zinc dilaurate 0.35 Parts of diethanolamine

5 Parts of ethyl glycol acetate

5 Parts of Solvesso 100

6 Parts of Xylene and 6.36 Parts of butyl acetate are added to 2.5 parts of a compound of formula 1a (described in Example 1) and 30 parts of Desmodur N 75 (from Bayer).

The homogenous mixture so formed is applied conventionally (according to the known 2 layer procedure) to a metallic or single pigment finish whilst both are still wet by spraying to form a layer having a thickness of 30 to 40 μm and the resulting coating is hardened over 20 minutes at 80° to 90°. The resulting 2K-PUR coating shows a good resistance to U.V. light and weathering.

APPLICATION EXAMPLE D

A single white pigmented finish of 14.30 Parts of Setamine US-132 BB70 (a 70% solution of a melamine resin from Synthese);

57.15 Parts of Setal 84 W-70 (a 70% solution of an alkyd resin from Synthese);

7.70 Parts of n-butanol;

1.85 Parts of butyl glycol acetate; and 9.50 Parts of titanium dioxide (Rutil type)

is added with 1.38 parts of the product of formula 1a (see Example 1).

The finish is conventionally applied to a grounded steel metal to which a filler of layer thickness 20 to 30 μm has been annealed, by spraying and after standing for 30 minutes at room temperature the steel metal surface is annealed at 120° C. for 30 minutes. The resulting coating shows very good resistance to U.V. light and weathering.

In Application Examples A to D instead of the product of formula 1a, an appropriate amount of the product of any one Examples 2 to 17 can be used.

What is claimed is:

1. A compound of formula I $$\left[ Y \right] \left[ \begin{array}{c} -C=N- \\ | \\ O-X \end{array} \right]_n Z \quad \text{I}$$

in which n is 1, 2 or 3;

Y is $C_{1-22}$alkyl or phenyl, unsubstituted or monosubstituted by phenyl and/or mono-, di- or tri-substituted by $C_{1-4}$alkyl, $C_{1-4}$alkoxy and halogen; or Y is

[thiophene and benzothiophene structures]

when n is 1, Z is $C_{1-22}$alkyl, uninterrupted or interrupted by —O— or phenyl, unsubstituted or substituted by 1 to 3 groups selected from $C_{1-4}$alkyl, $C_{1-4}$alkoxy and halogen and/or one group phenyl;

when n is 2, Z is $C_{1-22}$alkylene uninterrupted or interrupted by —O— or phenylene, unsubstituted or monosubituted by a $C_{1-4}$ alkyl, $C_{1-4}$ alkoxy or halogen group; and when n is 3, Z is a trivalent $C_{1-22}$alkane group or a group of the formula

[trisubstituted benzene structure]

X is a group of formula α, β, γ or δ

[structure α: benzophenone with HO, H, $R_4$]

[structure β: benzotriazole with HO, H, $R_4$]

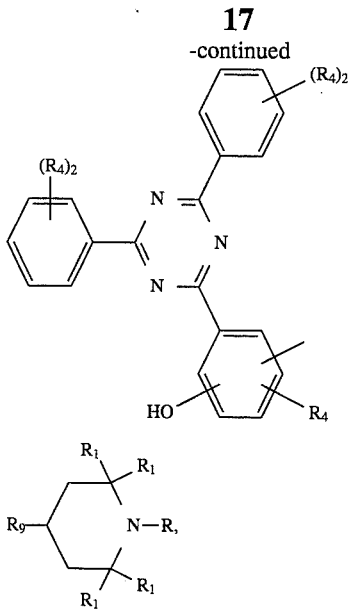

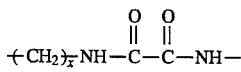

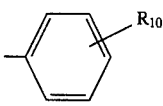

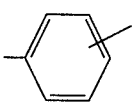

in which

R is hydrogen; oxygen; —OH; $C_{1-24}$alkyl; —O—CO—$C_{1-24}$alkyl; —O—$C_{1-24}$alkyl; —O—CO-phenyl or —$COR_5$;

where $R_5$ is —$C(R_3)$=$CH_2$, $C_{1-6}$alkyl, phenyl, —$COC_{1-24}$alkyl; —CO-phenyl, —$NR_7R_8$, —$COC_5H_5$, —$CH_2$—$C_6H_5$, —CO—$OC_{1-12}$alkyl or —COOH; $R_3$ is hydrogen or $C_{1-4}$alkyl, $R_7$ is hydrogen, $C_{1-12}$alkyl, $C_{5-6}$cycloalkyl, phenyl, phenyl-$C_{1-4}$alkyl or $C_{1-12}$alkylphenyl and $R_8$ is $C_{1-12}$alkyl or hydrogen, each $R_1$ independently, is —$CH_3$ or —$CH_2(C_{1-4}$alkyl) or both groups $R_1$ form a group —$(CH_2)_5$—;

each $R_2$, independently, is —$CH_3$ or —$CH_2(C_{1-4}$alkyl) or both groups $R_2$ form a group —$(CH_2)_5$—;

each $R_4$, independently is hydrogen, $C_{1-22}$alkyl, $C_{1-22}$alkoxy or halogen; and $R_9$ is a direct bond or the divalent bridging group according to the formula $$\text{--(CH}_2\text{)}_x\text{--NH--}\overset{\overset{\displaystyle O}{\|}}{C}\text{--}\overset{\overset{\displaystyle O}{\|}}{C}\text{--NH--}$$

wherein x is 1 to 8.

2. A compound according to claim 1 in which Z is Z' where Z', when n=1, is $C_{1-12}$alkyl or a group of the formula

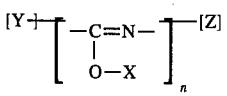

where Z', when n=2, is $C_{1-8}$alkylene or a group of the formula

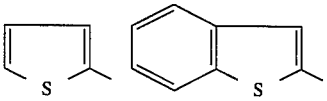

where Z', when n=3, is a group of the formula

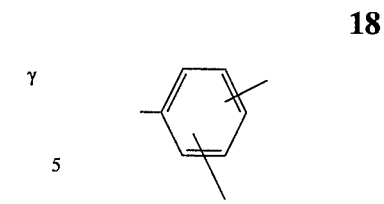

where $R_{10}$ is methyl, ethyl, methoxy, ethoxy, chloro or phenyl.

3. A compound according to claim 1 in which n is n' where n' is 1 or 2.

4. A compound according to claim 1 in which all groups $R_1$ and $R_2$ are —$CH_3$ and R is R' where R' is hydrogen, $C_{1-4}$alkyl or —CO—$R_5$', where $R_5$' is —CH=CH", $C_{1-4}$alkyl or —CO—O—$C_{1-4}$alkyl.

5. A compound according to claim 1 in which X is X' where X' is a group of formula γ defined in claim 1.

6. A compound of the formula

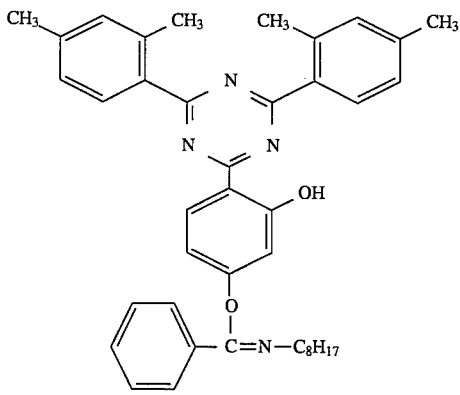

7. A composition comprising a polymeric lacquer material based on acrylic, alkyd and/or polyester resins, optionally crosslinked with melamine/formaldehyde resins, epoxide resins or polyisocyanates and, at least one compound according to claim 1.

8. A method for stabilizing a lacquer composition as defined in claim 7, comprising incorporating into the resin one or more compounds of formula I as defined in any one of claims 1 to 6.

9. A process for the preparation of a compound according to the formula $$[Y]\!\!-\!\!\left[\begin{array}{c}\text{--C=N--}\\|\\\text{O--X}\end{array}\right]_n\!\!-\!\![Z]$$

in which n is 1, 2 or 3;

Y is $C_{1-22}$alkyl or phenyl, unsubstituted or monosubstituted by phenyl and/or mono-, di- or tri-substituted by $C_{1-4}$alkyl, $C_{1-4}$alkoxy and halogen; or Y is when n is 1, Z is $C_{1-22}$alkyl, uninterrupted or interrupted by —O— or phenyl, unsubstituted or substituted by 1 to 3 groups selected from $C_{1-4}$alkyl, $C_{1-4}$alkoxy and halogen and/or one group phenyl;

when n is 2, Z is $C_{1-22}$alkylene uninterrupted or interrupted by —O— or phenylene, unsubstituted or monosubituted by a $C_{1-4}$alkyl, $C_{1-4}$alkoxy or halogen group; and when n is 3, Z is a trivalent $C_{1-22}$alkane group or a group of the formula

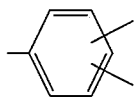

X is a group of formula α, β, γ or δ

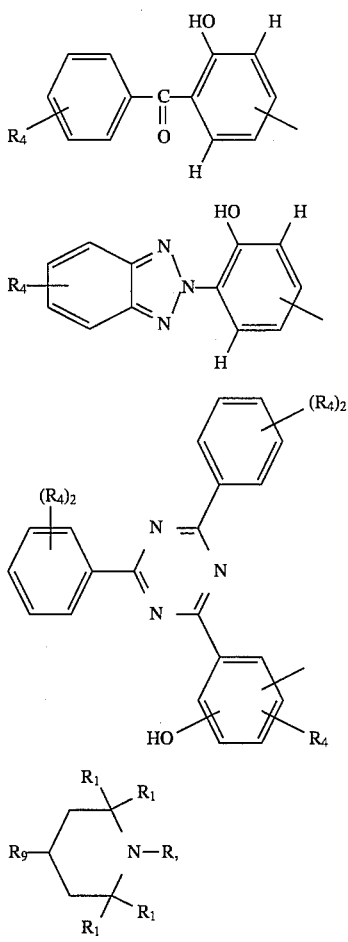

in which
R is hydrogen; oxygen; —OH; $C_{1-24}$alkyl; —O—CO—$C_{1-24}$alkyl; —O—$C_{1-24}$alkyl; —O—CO—phenyl or —COR$_5$;

where $R_5$ is —C($R_3$)=CH$_2$, $C_{1-6}$alkyl, phenyl, —COC$_{1-24}$alkyl; —CO-phenyl, —NR$_7$R$_8$, —COC$_5$H$_5$, —CH$_2$—C$_6$H$_5$, —CO—OC$_{1-12}$alkyl or —COOH; $R_3$ is hydrogen or $C_{1-4}$alkyl, $R_7$ is hydrogen, $C_{1-12}$alkyl, $C_{5-6}$cycloalkyl, phenyl, phenyl-$C_{1-4}$alkyl or $C_{1-12}$alkylphenyl and $R_8$ is $C_{1-12}$alkyl or hydrogen, each $R_1$ independently, is —CH$_3$ or —CH$_2$($C_{1-4}$alkyl) or both groups $R_1$ form a group —(CH$_2$)$_5$—;

each $R_2$, independently, is —CH$_3$ or —CH$_2$($C_{1-4}$alkyl) or both groups $R_2$ form a group —(CH$_2$)$_5$—;

each $R_4$, independently is hydrogen, $C_{1-22}$alkyl, $C_{1-22}$alkoxy or halogen; and $R_9$ is a direct bond or the divalent bridging group according to the formula

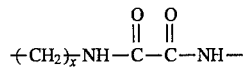

wherein x is 1 to 8;
which process comprises the steps of:
reacting n moles of a compound of formula II

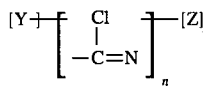 (II)

with n moles of a compound of formula III

X—OH   (III)

in which n is 1, 2 or 3, and
X is a group of formula α, β, γ or δ.
10. A composition comprising:
a polymer, and,
at least one compound according to claim 1.
11. A polymer composition comprising:
at least one compound according to claim 1.
12. A process for stabilizing a lacquer composition selected from the group consisting of: acrylic resin based lacquer resins, alkyd based lacquer resins, and polyester based lacquer resins, which includes the process step of:
adding a stabilizing effective amount of at least one compound according to claim 1 to the lacquer composition.
13. A composition comprising:
a lacquer composition selected from the group consisting of: acrylic resin based lacquer resins, alkyd based lacquer resins, and polyester based lacquer resins, and;
at least one compound according to claim 1.

* * * * *